(12) United States Patent
Guo et al.

(10) Patent No.: US 12,734,027 B2
(45) Date of Patent: Sep. 15, 2026

(54) INTRAOCULAR LENS

(71) Applicant: MICROPORT VISIONPOWER MEDTECH (SHANGHAI) CO.LTD, Shanghai (CN)

(72) Inventors: Moqiang Guo, Shanghai (CN); Hongliu Wu, Shanghai (CN); Qiou Chen, Shanghai (CN); Jie Zhang, Shanghai (CN); Zhaohua Chang, Shanghai (CN)

(73) Assignee: MICROPORT VISIONPOWER MEDTECH (SHANGHAI) CO.LTD, Shanghai (CN)

( * ) Notice: Subject to any disclaimer, the term of this patent is extended or adjusted under 35 U.S.C. 154(b) by 296 days.

(21) Appl. No.: 18/293,261

(22) PCT Filed: Jan. 4, 2022

(86) PCT No.: PCT/CN2022/070079

§ 371 (c)(1),
(2) Date: Jan. 29, 2024

(87) PCT Pub. No.: WO2023/005152

PCT Pub. Date: Feb. 2, 2023

(65) Prior Publication Data

US 2024/0335276 A1 Oct. 10, 2024

(30) Foreign Application Priority Data

Jul. 29, 2021 (CN) ......................... 202110860679.1

(51) Int. Cl.
*A61F 2/16* (2006.01)

(52) U.S. Cl.
CPC .......... *A61F 2/1618* (2013.01); *A61F 2/1654* (2013.01); *A61F 2250/0037* (2013.01);
(Continued)

(58) Field of Classification Search
CPC .................. A61F 2/1618; A61F 2/1654; A61F 2250/0037; A61F 2250/0053; G02C 2202/20; G02B 5/1876; G02B 27/4205
See application file for complete search history.

(56) References Cited

U.S. PATENT DOCUMENTS 5,017,000 A 5/1991 Cohen
2007/0182917 A1 8/2007 Zhang et al.
(Continued)

FOREIGN PATENT DOCUMENTS

CN 102395906 A 3/2012
CN 107920889 A 4/2018
(Continued)

OTHER PUBLICATIONS

Extended European Search Report issued for European Patent Application No. 22847774.1, dated Jun. 17, 2025, 11 pages.
(Continued)

*Primary Examiner* — Javier G Blanco
(74) *Attorney, Agent, or Firm* — HSML P.C.

(57) ABSTRACT

An intraocular lens has a lens body. At least one side surface of the lens body is provided with a focus determination diffraction area and a focus offset diffraction area. The focus determination diffraction area comprises at least two focus determination diffraction structures of different heights. The focus determination diffraction structures of different heights are alternately arranged to provide the intraocular lens with focuses which respectively correspond to distant vision, intermediate vision and near vision. The focus offset diffraction area comprises focus offset diffraction structures which corresponds to the focus determination diffraction structures. The height ratio of the at least one focus offset diffraction structure to a corresponding focus determination diffraction structure is 1.1 to 1.3 or 0.8 to 0.95. The focus
(Continued)

offset diffraction structures provide the intraocular lens with offset focuses.

11 Claims, 5 Drawing Sheets

(52) U.S. Cl.
CPC ................. *A61F 2250/0039* (2013.01); *A61F 2250/0053* (2013.01)

(56) References Cited

U.S. PATENT DOCUMENTS

2017/0209259 A1 7/2017 Choi et al.
2017/0252151 A1 9/2017 Mackool
2018/0092739 A1* 4/2018 Pagnoulle ............. A61F 2/1654
2018/0147052 A1* 5/2018 Hong ................. G02B 27/4205
2018/0368972 A1 12/2018 Rosen et al.

FOREIGN PATENT DOCUMENTS

CN 108066046 A 5/2018
CN 108836571 A 11/2018
CN 110753528 A 2/2020
CN 111417364 A 7/2020
CN 111971613 A 11/2020
CN 112004499 A 11/2020
CN 112147797 A 12/2020
CN 112198577 A 1/2021
CN 113331994 A 9/2021
WO WO-2018150236 A1 * 8/2018 ........... A61F 2/1618
WO WO-2019130031 A1 * 7/2019 ........... A61F 2/1618
WO 2020132703 A1 6/2020
WO 2021089178 A1 5/2021

OTHER PUBLICATIONS

Search Report issued for Chinese Patent Application No. 202110860679.1, dated Sep. 13, 2021, 3 pages.
International Search Report issued for International Patent Application No. PCT/CN2022/070079, Date of mailing: Apr. 6, 2022, 10 pages including English translation.
Written Opinion issued for International Patent Application No. PCT/CN2022/070079, Date of mailing: Apr. 6, 2022, 7 pages including English machine translation.

* cited by examiner

INTRAOCULAR LENS

CROSS REFERENCE TO RELATED DISCLOSURE

The present application is a US national stage application of PCT international application PCT/CN2022/070079, filed on Jan. 4, 2022, which claims priority to Chinese Patent Disclosure with No. 202110860679.1, entitled “Intraocular Lens”, and filed on Jul. 29, 2021, the content of which is expressly incorporated herein by reference in its entirety.

TECHNICAL FIELD

The present disclosure relates to the field of medical devices, and particularly to an intraocular lens.

BACKGROUND

The natural lenses of the human eyes are adaptive lenses which are clear and transparent and can change the focal length autonomously. However, with age or bad eye habits, the natural lenses easily become cloudy, thereby greatly reducing the vision of the human eyes and even causing blindness. With the development of phacoemulsification equipment, micro-incision intraocular lens replacement is gradually mastered in the industry, by which the cloudy natural lens is replaced with a soft intraocular lens, thereby improving the vision of the human eye and even achieving cataract recovery.

Furthermore, with the advent of the era of refractive intraocular lens surgery, it is difficult for the monofocal intraocular lens to meet patients’ requirements for good vision at all visual distances after surgery. In order to realize the patient’s desire to remove glasses after surgery, the multifocal intraocular lens is created.

However, for traditional multifocal intraocular lenses, although they can provide patients with clear vision at three visual distances, i.e., far visual distance, middle visual distance and near visual distance, the depth of field at the corresponding visual distance is shallow. That is, when the patient’s visual distance switches between the far visual distance and the middle visual distance or between the middle visual distance and near visual distance, the vision may have a significant sudden loss, which greatly reduces the patient’s postoperative experience.

SUMMARY

In view of this, it is necessary to provide an intraocular lens.

An intraocular lens includes: a lens body, at least one side surface of the lens body being provided with a focusing diffraction region and a shifting diffraction region, the focusing diffraction region includes at least two types of focusing diffraction structures with different heights, and the focusing diffraction structures with different heights are arranged alternately to provide the intraocular lens with focuses corresponding to a far distance vision, a middle distance vision and a near distance vision respectively; the shifting diffraction region includes shifting diffraction structures corresponding to the focusing diffraction structures; and a height ratio of at least one type of the shifting diffraction structures to one corresponding type of the focusing diffraction structures ranges from 1.1 to 1.3, or from 0.80 to 0.95, the shifting diffraction structure is configured to provide a shift focus for the intraocular lens, the shift focus is located in a range between the focus corresponding to the far distance vision and the focus corresponding to the middle distance vision, and/or in a range between the focus corresponding to the middle distance vision and the focus corresponding to the near distance vision.

In an embodiment, one type of the focusing diffraction structures is configured to provide a far distance visual focus corresponding to the far distance and/or a middle distance visual focus corresponding to the middle distance vision, and a height ratio of one corresponding type of the shifting diffraction structures to the focusing diffraction structure providing the far distance visual focus and/or the middle distance visual focus ranges from 1.1 to 1.3.

In an embodiment, one type of the focusing diffractive structures is configured to provide a middle distance visual focus corresponding to the middle distance vision and/or a near distance visual focus corresponding to the near distance vision, and a height ratio of the one corresponding type of the shifting diffraction structures to the focusing diffraction structure providing the middle distance visual focus and/or the near distance visual focus ranges from 0.80 to 0.95.

In an embodiment, the at least two types of focusing diffraction structures with different heights include a first focusing diffraction structure and a second focusing diffraction structure, a first diffraction order of the first focusing diffraction structure is configured to provide a far distance visual focus for the far distance vision, a second diffraction order of the first focusing diffraction structure is paired with a first diffraction order of the second focusing diffraction structure to provide a middle distance visual focus for the middle distance vision, and a third diffraction order of the first focusing diffraction structure is configured to provide a near distance visual focus for the near distance vision.

In an embodiment, the at least two types of focusing diffraction structures with different heights include a first focusing diffraction structure and a second focusing diffraction structure, a first diffraction order of the first focusing diffraction structure is paired with a first diffraction order of the second focusing diffraction structure to provide a far distance visual focus for the far distance vision, a second diffraction order of the first focusing diffraction structure is configured to provide a middle distance visual focus for the middle distance vision, a third diffraction order of the first focusing diffraction structure is configured to provide a near distance visual focus for the near distance vision.

In an embodiment, the at least two types of focusing diffraction structures with different heights include a first focusing diffraction structure and a second focusing diffraction structure, a first diffraction order of the first focusing diffraction structure is configured to provide a far distance visual focus for the far distance vision, a second diffraction order of the first focusing diffraction structure is configured to provide a middle distance visual focus for the middle distance vision, and a third diffraction order of the first focusing diffraction structure is paired with a first diffraction order of the second focusing diffraction structure to provide a near distance visual focus for the near distance vision.

In an embodiment, the at least two types of focusing diffraction structures with different heights include a first focusing diffraction structure and a second focusing diffraction structure, a first diffraction order of the first focusing diffraction structure is paired with a first diffraction order of the second focusing diffraction structure to provide a far distance visual focus for the far distance vision, a second diffraction order of the first focusing diffraction structure is paired with a second diffraction order of the second focusing diffraction structure to provide a middle distance visual focus for the middle distance vision, and a third diffraction order of the first focusing diffraction structure is paired with a third diffraction order of the second focusing diffraction structure to provide a near distance visual focus for the near distance vision.

In an embodiment, the at least one type of the shifting diffraction structures includes a first shifting diffraction structure and a second shifting diffraction structure; the first shifting diffraction structure corresponds to the first focusing diffraction structure, and a height ratio of the first shifting diffraction structure to the first focusing diffraction structure ranges from 1.1 to 1.3; the second shifting diffraction structure corresponds to the second focusing diffraction structure, and a height ratio of the second shifting diffraction structure to the second focusing diffraction structure ranges from 1.1 to 1.3.

In an embodiment, the at least one type of the shifting diffraction structures further includes a third shifting diffraction structure, a height ratio of the third shifting diffraction structure to the first focusing diffraction structure, or to the second focusing diffraction structure ranges from 0.80 to 0.95.

In an embodiment, the shifting diffraction region includes at least two types of shifting diffraction structures with different heights, and the shifting diffraction structures with different heights are arranged alternately in sequence.

In an embodiment, the focusing diffraction structure and the shifting diffraction structure are respectively rotationally symmetrical with respect to an optical axis of the lens body, and a ratio of an area of the shifting diffraction region to an area of the focusing diffraction structure ranges from 0.21 to 0.33; the area of the focusing diffraction region is a sum of areas of the focusing diffraction structures, and an area of each of the focusing diffraction structures is represented as $\pi(rj^2-ri^2)$, where ri denotes the minimum distance from the focusing diffraction structure to the optical axis, rj denotes the maximum distance from the same focusing diffraction structure to the optical axis; and the area of the shifting diffraction region is a sum of areas of the shifting diffraction structures, and an area of each of the shifting diffraction structures is represented as $\pi(rl^2-rk^2)$, where rk denotes the minimum distance from the shifting diffraction structure to the optical axis, and rl is the maximum distance from the same shifting diffraction structure to the optical axis.

In an embodiment, the focusing diffraction region is located at a periphery of the shifting diffraction region, and an inner ring of the focusing diffraction region is connected to an outer ring of the shifting diffraction region, and the shifting diffraction region includes a shifting diffraction structure through which the optical axis of the lens body passes and a shifting diffraction structure spaced apart from the optical axis.

In an embodiment, the shifting diffraction structure spaced apart from the optical axis is provided with a second step surface facing the optical axis and a second diffraction surface facing away from the optical axis, one end of the second step surface of the shifting diffraction structure is configured to be connected to the second diffraction surface of the shifting diffraction structure, and the other end is configured to be connected to a diffraction surface of an adjacent focusing diffraction structure or an adjacent shifting diffraction structure, there exists an abrupt change in the surface type at a connection between surfaces, and the shifting diffraction structure through which the optical axis of the lends body passes is provided with a second diffraction surface.

In an embodiment, an outer ring radius of the shifting diffraction region is less than or equal to 1.5 mm, and an outer ring radius of the focusing diffraction region is less than or equal to 3 mm.

In an embodiment, the shifting diffraction region is located at a periphery of the focusing diffraction region, an inner ring of the shifting diffraction region is connected to an outer ring of the focusing diffraction region, and the focusing diffraction region includes a focusing diffraction structure through which the optical axis passes and a focusing diffraction structure spaced apart from the optical axis.

In an embodiment, the focusing diffraction structure spaced apart from the optical axis is provided with a first step surface facing the optical axis and a first diffraction surface facing away from the optical axis, one end of the first step surface of the focusing diffraction structure is configured to be connected to the first diffraction surface of the focusing diffraction structure, the other end is configured to be connected to a diffraction surface of an adjacent focusing diffraction structure or an adjacent shifting diffraction structure, there exists an abrupt change in the surface type at a connection between surfaces, the focusing diffraction structure through which the optical axis passes is provided with a first diffraction surface.

In an embodiment, an outer ring radius of the focusing diffraction region is greater than or equal to 2.5 mm, and an outer ring radius of the shifting diffraction region is less than or equal to 3 mm.

In an embodiment, a focal power of the lens body ranges from −10 D to +36 D, an additional optical power of the focusing diffraction structure for the near distance vision ranges from +3.00 D to +4.34 D, and an additional optical power of the focusing diffraction structure for the middle distance vision ranges from +1.50 D to +2.17 D.

In an embodiment, there exists an integer multiple relationship among focal lengths corresponding to the first diffraction orders of the focusing diffraction structures with different heights.

In an embodiment, the intraocular lens may further include a pair of haptics connected to the lens body.

The details of one or more embodiments of the present disclosure are set forth in the accompanying drawings and the description below. Other features, purposes and advantages of the present disclosure will become obvious from the description, drawings and claims.

BRIEF DESCRIPTION OF THE DRAWINGS

In order to more clearly illustrate the technical solution in the embodiment of the present disclosure, the accompanying drawings required in the description of the embodiments will be briefly introduced below. Obviously, the drawings in the following description are merely some embodiments of the present disclosure. The ordinary skilled in the art can obtain drawings of other embodiments according to these drawings without any creative efforts.

In the drawings.

Figure 1:
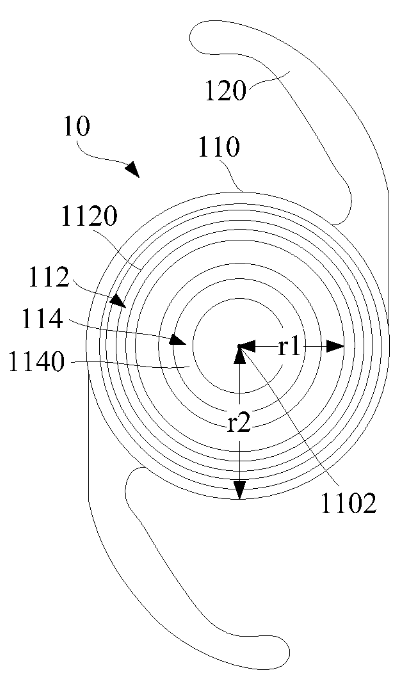
FIG. 1 is a front view of an intraocular lens according to an embodiment of the present disclosure.

10, intraocular lens; 110, lens body; 1102, optical axis; 112, focusing diffraction region; 1120, focusing diffraction structure; 112*a*, first step surface; 112*b*, first diffraction surface; 1121, first focusing diffraction structure; 1122, second focusing diffraction structure; 114, shifting diffraction region; 1140, shifting diffraction structure; 114*a*, second step surface; 114*b*, second diffraction surface; 1141, first shifting diffraction structure; 1142, second shifting diffraction structure; 120, haptics.

DETAILED DESCRIPTION

In order to make the above purpose, features and advantages of the present disclosure more obvious and easier to understand, the specific implementation modes of the present disclosure will be described in detail below with reference to the accompanying drawings. In the following description, numerous specific details are set forth in order to provide thorough understanding of the present disclosure. However, the present disclosure may also be implemented in many other modes different from those described here. Those skilled in the art can make similar improvements without departing from the connotation of the present disclosure. Therefore, the present disclosure is not limited by the specific embodiments disclosed below.

In the description of the present disclosure, it should be understood that the orientation or positional relationship indicated by terms "center", "longitudinal", "transverse", "length", "width", "thickness", "upper", "lower", "front", "rear", "left", "right", "vertical", "horizontal", "top", "bottom", "inside", "outside", "clockwise", "counterclockwise", "axial direction", "radial direction", "circumferential direction", etc., is based on the orientation or positional relationship shown in the drawings, and is only for the convenience of describing the present disclosure and simplifying the description, rather than indicating or implying that the described device or component must have a specific orientation, or be constructed and operate in a specific orientation, Therefore, such orientation or positional relationship is not to be construed as a limitation on the present disclosure.

In addition, the terms "first" and "second" are merely used for descriptive purposes and cannot be understood as indicating or implying relative importance or implicitly indicating the quantity of indicated technical features. Therefore, features defined with "first" and "second" may explicitly or implicitly include at least one of these features. In the description of the present disclosure, "plurality" means at least two, such as two, three, etc., unless otherwise expressly and specifically limited.

In the present disclosure, unless otherwise clearly stated and limited, the terms "installation", "connection", "coupling", "fixing" and other terms should be understood in a broad sense. For example, it may be a fixed connection or a detachable connection, or formed in one piece. It may also be a mechanical connection or an electrical connection. It may be a direct connection or an indirect connection through an intermediate medium. It can be an internal communication or an interactive relationship between two components, unless otherwise specified restrictions. For those of ordinary skill in the art, the specific meanings of the above terms in the present disclosure can be understood according to specific conditions.

In the present disclosure, unless otherwise expressly stated and limited, if a first feature is described as being "above" or "below" a second feature, it may mean that the first feature is directly in contact with the second feature, or the first feature is in contact with the second feature through an intermediate medium. Furthermore, if a first feature is described as being "above", "on" or "upper" the second feature, it may mean that the first feature is directly above or diagonally above the second feature, or it may simply mean that the first feature is higher than the second feature in level. If a first feature is described as being "below", "under" or "beneath" the second feature, it may mean that the first feature is directly below or diagonally below the second feature, or it may simply mean that the first feature is lower than the second feature in level.

It should be noted that when a component is described as being "fixed to" or "provided on" another component, the component may be directly on the other element or there may exist an intermediate component. When a component isdescribed as being "connected" to another component, the component may be directly connected to the other component or there may exist an intermediate component. The terms "vertical", "horizontal", "upper", "lower", "left", "right" and other similar expressions used herein are merely for illustrative purposes and do not represent the only implementation mode. With age or bad eye habits, the lens of the human eye may easily become cloudy, which leads to decreased or even loss of vision. With the development of lens replacement technology, the technology of surgically inserting a multifocal intraocular lens into the original human eye lens to improve vision is implemented. However, for the conventional multifocal intraocular lens, although it can provide the patient with clear vision at three visual distances, i.e., the far visual distance, the middle visual distance and the near visual distance, the depth of field at the corresponding visual distances is shallow. Accordingly, when the patient's visual distance switches between the far visual distance and the middle visual distance or between the middle visual distance and the near visual distance, the vision may have a significant sudden loss, which greatly reduces the patient's postoperative experience. To this end, in the embodiments of the present disclosure, an intraocular lens is provided to address the problem of sudden loss of vision during switching of visual distances.

Figure 2:
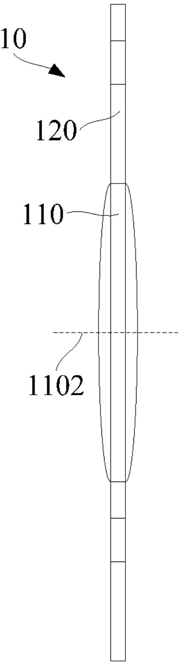
FIG. 2 is a side view of an intraocular lens according to an embodiment of the present disclosure.

Referring to FIGS. 1 and 2, in an embodiment of the present disclosure, an intraocular lens 10 is provided, which includes a lens body 110. At least one side surface of the lens body 110 is provided with a focusing diffraction region 112 and a shifting diffraction region 114. The focusing diffraction region 112 includes at least two types of focusing diffraction structures 1120 with different heights. Diffraction structures with the same height are regarded as the same type of structure. The different types of focusing diffraction structures 1120 are arranged alternately, thereby providing the intraocular lens 10 with focuses respectively corresponding to a far distance vision, a middle distance vision and a near distance vision. The alternating arrangement of the focusing diffraction structures 1120 with different heights facilitates partial overlap of diffraction orders of the focusing diffraction structures 1120 with different heights, thereby enhancing the light energy at a focus corresponding to an expected visual distance, and then acquiring an expected multifocal lens. That is, the alternating arrangement of at least two types of focusing diffraction structures 1120 with different heights helps the patient obtain a clear view at the expected visual distance. It should be noted that the focusing diffraction region 112 may be a continuous region on a surface of the lens body 110. Alternatively, the focusing diffraction region 112 may be divided into a number of sub-regions to be interspersed with the shifting diffraction region 114, while at least two types of focusing diffraction structures 1120 with different heights are located in the same region and alternately arranged in a regular order. In addition, due to the precision limitation of the manufacturing process, it is unavoidable that slight height differences may exist in the actual manufacturing process for diffraction structures with the same height in theory. However, when a ratio of an actual height of each of two diffraction structures to a theoretical height ranges from 0.99 and 1.01, the two diffractive structures can be regarded as being designed as the same height.

For a focusing diffraction structure with a certain height, incident light with a designed wavelength may form a plurality of diffraction orders due to coherence enhancement after passing through the focusing diffraction structure and a subsequent corresponding structure of the lens body 110. The formed maximum optical path difference of the incident light corresponding to a first diffraction order focus is equal to a design wavelength, the formed maximum optical path difference of the incident light corresponding to a second diffraction order focus is twice the design wavelength, the formed maximum optical path difference of the incident light corresponding to a third diffraction order focus is three times the design wavelength, and so on. In addition, first diffraction order focuses of the focusing diffraction structures with the same height overlap with each other, and second diffraction order focuses of the focusing diffraction structures with the same height overlap with each other, and so on.

Further, the shifting diffraction region 114 includes a shifting diffraction structure 1140 corresponding to the focusing diffraction structure 1120. A height ratio of at least one type of shifting diffraction structure 1140 to the corresponding type of focusing diffraction structure 1120 ranges from 1.1 to 1.3, or from 0.80 to 0.95. The shifting diffraction structure 1140 provides a shift focus for the intraocular lens 10. The shift focus is located in a range between the focus corresponding to the far distance vision and the focus corresponding to the middle distance vision, and/or is located in a range between the focus corresponding to the middle distance vision and the focus corresponding to the near distance vision. Generally speaking, in the embodiments of the present disclosure, shifting diffraction structures 1140 with a single height may be designed, or two or more types of shifting diffraction structures 1140 with different heights may be designed. However, each type of shifting diffraction structure 1140 with a height corresponds to one type of focusing diffraction structure 1120 with a height. The shifting diffraction structure 1140 and the focusing diffraction structure 1120, which have a corresponding relationship therebetween, exhibit any one of the heigh ratios as described above. For example, in an embodiment, a focusing diffraction structure 1120 with a specified height may correspond to shifting diffraction structures 1140 with two heights, a height ratio of the shifting diffraction structure 1140 with one height to the focusing diffraction structure 1120 may range from 1.1 to 1.3, and a height ratio of the shifting diffraction structure 1140 with the other height to the focusing diffraction structure 1120 may range from 0.80 to 0.95. Correspondingly, the shifting diffraction region 114 in some embodiments may also be divided into a number of sub-regions arranged at intervals, each of which includes at least one shifting diffraction structure 1140. Specifically, in some embodiments, the height ratio of the shifting diffraction structure 1140 to the corresponding focusing diffraction structure 1120 may be 1.13, 1.15, 1.18, 1.2, 1.26 or 1.28, or may also be 0.82, 0.85, 0.88, 0.91 or 0.93.

In the intraocular lens 10 with the above design provided by the embodiment of the present disclosure, at least two types of focusing diffraction structures 1120 with different heights are provided and alternately arranged, to provide the intraocular lens 10 with expected focuses corresponding to the expected far distance vision, middle distance vision and near distance vision respectively. It can provide at least three focuses, or four or more focuses, so that the patient can have good vision at at least three corresponding expected visual distances. Further, by providing the shifting diffraction structure 1140 corresponding to the focusing diffraction structure 1120, the height ratio of the shifting diffraction structure 1140 to the corresponding focusing diffraction structure 1120 is controlled in the range from 1.1 to 1.3 or from 0.80 to 0.95, so that the shifting diffraction structure 1140 can provide a shift focus for the intraocular lens 10, to allow the shift focus to be located in the range between the focus corresponding to the far distance vision and the focus corresponding to the middle distance vision, and/or located in the range from the focus corresponding to middle distance vision to the focus corresponding to the near distance vision. Accordingly, the light energy originally concentrated at the corresponding expected visual distance is dispersed in an expected direction to fill in the missing light energy between the far visual distance and the middle visual distance, and/or to fill in the missing light energy between the middle visual distance and the near visual distance. Through the above design, the vision of the patient is not prone to a sudden loss in the process of switching the patient's visual distance between the far visual distance and the middle visual distance, and/or between the middle visual distance and the near visual distance, thereby providing the patient with the smooth transition of vision in the switching process of different visual distances, improving the vision balance of the patient among the expected far, middle and near visual distances, and accordingly improving the postoperative experience of the patient.

It should be noted that, for the focusing diffraction structure 1120 capable of providing the far distance visual focus corresponding to the far distance vision, the middle distance visual focus corresponding to the middle distance vision, and the near distance visual focus corresponding to the near distance vision, when the corresponding shifting diffraction structure 1140 is provided, and the height ratio of the shifting diffraction structure 1140 to the focusing diffraction structure 1120 ranges from 1.1 to 1.3, the shifting diffraction structure 1140 can provide the shift focus in the range between the far distance visual focus and the middle distance visual focus, and provide the shift focus in the range between the middle distance visual focus and the near distance visual focus. When the height ratio of the shifting diffraction structure 1140 to the focusing diffraction structure 1120 ranges from 0.80 to 0.95, the shifting diffraction structure 1140 can also provide the shift focuses in the range between the far distance visual focus and the middle distance visual focus, and provide the shift focus in the range between the middle distance visual focus and the near distance visual focus. However, when a focusing diffraction structure 1120 only provides a middle distance visual focus, and there exists a corresponding shifting diffraction structure 1140 with a height ratio of the shifting diffraction structure 1140 to the focusing diffraction structure 1120 ranging from 1.1 to 1.3, the shifting diffraction structure 1140 may only provide the shift focus in the range between the middle distance visual focus and the near distance visual focus. When the height ratio of the shifting diffraction structure 1140 to the focusing diffraction structure 1120 ranges from 0.80 to 0.95, the shifting diffraction structure 1140 may only provide the shift focus in the range between the far distance visual focus and the middle distance visual focus.

In structure, the intraocular lens 10 may be regarded as having a number of focusing diffraction structures 1120 and a number of shifting diffraction structures 1140 provided on one side surface of the lens body 110, and the one side surface can serve as a virtual reference surface. In some embodiments, the number of the focusing diffraction structures 1120 may be 14 to 17. The number of the shifting diffraction structures 1140 may be 4 to 6. In some embodiments, in a focusing diffraction region 112, there exists focusing diffraction structures 1120 with different heights arranged alternately, and some focusing diffraction structures 1120 with the same height may also be arranged adjacently. For the shifting diffraction region 114, when there exists shifting diffraction structures 1140 with different heights, some of the shifting diffraction structures 1140 with different heights are arranged alternately, and some of the shifting diffraction structures 1140 with the same height may be arranged adjacently.

In some embodiments, for the structure of the lens body 110, the opposite surfaces of the lens body 110 along its own optical axis 1102 can be configured with surface types such as a convex-convex type, a convex-flat type, a flat-convex type, etc., so that the lens body 10 itself can provide the intraocular lens 10 with a focal power, for example, from −10 D to +36 D. An additional focal power provided by each focusing diffraction structure 1120 for the near distance vision ranges from +3.00 D to +4.34 D, and the additional focal power for the middle distance vision ranges from +1.50 D to +2.17 D. In addition, for the structures of the focusing diffraction structure 1120 and the shifting diffraction structure 1140, each of which should be rotationally symmetrical with respect to the optical axis 1102 of the lens body 110 under an ideal manufacturing process, and the surface of the lens body 110 may be aspherical.

Figure 3:
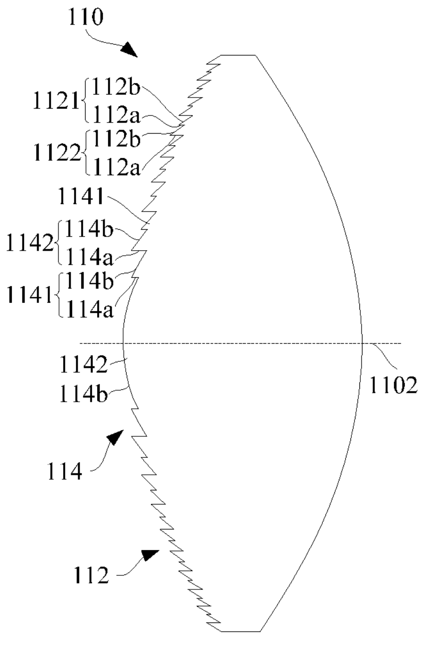
FIG. 3 is a cross-sectional view of an intraocular lens through an optical axis according to an embodiment of the present disclosure.
Figure 4:
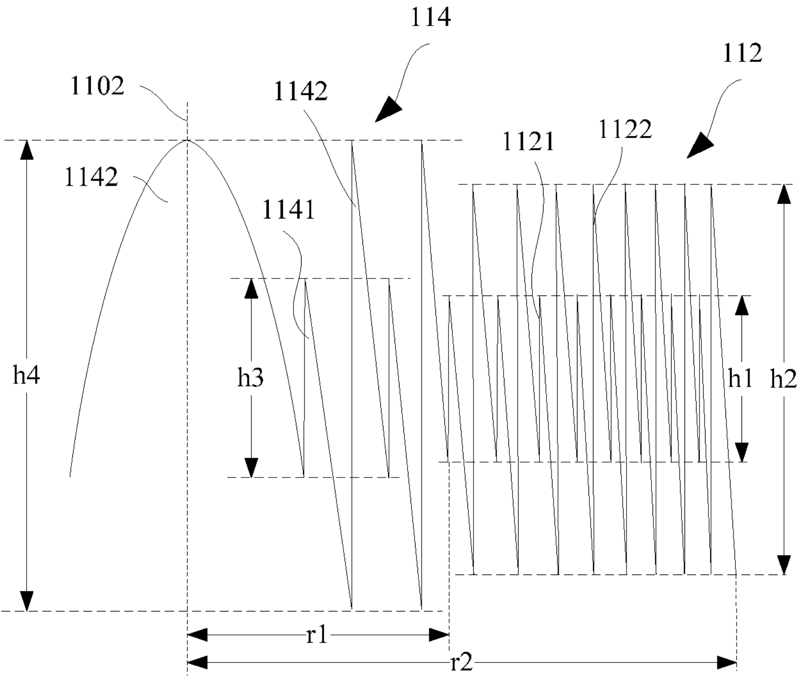
FIG. 4 is a schematic diagram illustrating a partial arrangement of a focusing diffraction structure and a shifting diffraction structure of an intraocular lens according to an embodiment of the present disclosure.

Referring to FIGS. 3 and 4, in some embodiments, when the optical axis 1102 passes through the shifting diffraction region 114, the shifting diffraction region 114 then includes a shifting diffraction structure 1140 through which the optical axis 1102 passes and a shifting diffraction structure 1140 spaced apart from the optical axis 1102. The shifting diffraction structure 1140 spaced apart from the optical axis 1102 has a second step surface **114*a* facing the optical axis 1102 and a second diffraction surface 114*b* facing away from the optical axis 1102. One end of the second step surface 114*a* of the shifting diffraction structure 1140 is connected to the second diffraction surface 114*b* of the shifting diffraction structure 1140, and the other end is connected to a diffraction surface of an adjacent diffraction structure (such as an adjacent focusing diffraction structure 1120 or adjacent shifting diffraction structure 1140). There is an abrupt change in surface type at the connection between the surfaces. Generally, the second step surface 114*a* is parallel to the optical axis 1102, and the height of the shifting diffraction structure 1140 spaced apart from the optical axis 1102 is represented by the height of the second step surface 114*a*. The second diffraction surface 114*b* is a curved surface, and the second diffraction surface 114*b* is configured to refract incident light to obtain a desired focal length. On the other hand, the shifting diffraction structure 1140 through which the optical axis 1102 passes only has the second diffraction surface 114*b*, and the height of the shifting diffraction structure 1140 is equal to a difference (referring to the height h4 in FIG. 4) value between the highest point of the second diffraction surface 114*b* and the surface of the lens body 110 with the shifting diffraction structure 1140 in a direction parallel to the optical axis 1102**.

In other embodiments, when the optical axis 1102 passes through the focusing diffraction region 112, the focusing diffraction region 112 may include a focusing diffraction structure 1120 through which the optical axis 1102 passes and a focusing diffraction structure 1120 spaced apart from the optical axis 1102. The focusing diffraction structure 1120 spaced apart from the optical axis 1102 has a first step surface **112*a* facing the optical axis 1102 and a first diffraction surface 112*b* away from the optical axis 1102. One end of the first step surface 112*a* of the focusing diffraction structure 1120 is connected to the first diffraction surface 112*b* of the focusing diffraction structure 1120, and the other end is connected to a diffraction surface of an adjacent diffraction structure (such as an adjacent focusing diffraction structure 1120 or adjacent shifting diffraction structure 1140). There exists an abrupt change in the surface type at the connection between the surfaces. Generally, the first step surface 112*a* is parallel to the optical axis 1102, and the height of the focusing diffraction structure 1120 spaced apart from the optical axis 1102 is the height of the first step surface 112*a*. The first diffraction surface 112*b* is a curved surface, and the first diffraction surface 112*b* is configured to refract incident light to obtain the desired focal length. On the other hand, the focusing diffraction structure 1120 through which the optical axis 1102 passes only has the first diffraction surface 112*b*, and the height of the focusing diffraction structure 1120 is a difference value between the highest point of the first diffraction surface 112*b* and the surface of the lens body 110 provided with the focusing diffraction structure 1120 in the direction parallel to the optical axis 1102**.

Furthermore, it should be noted that the light rays within the expected depth of field range of the far visual distance may converge at the far distance visual focus after being adjusted by the intraocular lens 10. The position of the far distance visual focus depends on a position formed in an image space of the intraocular lens 10 at which the light rays within the expected depth of field range of the far visual distance have the maximum light energy. The positions of the middle distance visual focus and the near distance visual focus are defined similarly.

Figure 5:
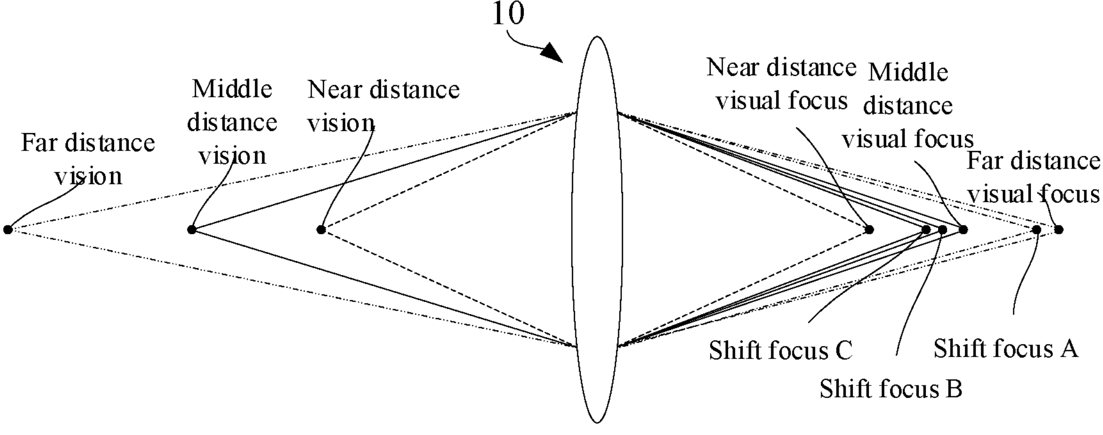
FIG. 5 is a schematic diagram illustrating relative positions of three focuses and shift focuses of the intraocular lens according to the embodiment of FIG. 4.

Referring to FIGS. 4 and 5, in an embodiment of the present disclosure, a solution for distributing shift focuses in the range between the far distance visual focus and the middle distance visual focus and/or in the range between the middle distance visual focus and the near distance visual focus. Specifically, a focusing diffraction structure 1120 provides a far distance visual focus corresponding to the far distance vision and/or a middle distance visual focus corresponding to the middle distance vision, and a height ratio of a shifting diffraction structure 1140 to the focusing diffraction structure 1120 providing the far distance visual focus corresponding to the far distance vision and/or the middle distance visual focus corresponding to the middle distance vision ranges from 1.1 to 1.3, for example, the height ratio may be equal to 1.13, 1.15, 1.18, 1.2, 1.26 or 1.28. The above design may allow the shift focus generated by the shifting diffraction structure 1140 to be located in the range between the focus corresponding to the far distance vision and the focus corresponding to the middle distance vision, and/or allow the shift focus to be located in the range between the focus corresponding to the middle distance vision and the focus corresponding to the near distance vision, so that partial light energy originally concentrated around the far distance visual focus can be effectively diffused towards the middle distance visual focus, and/or the light energy around the middle distance visual can be effectively diffused towards the near distance visual focus, thereby the vision of the patient is not prone to sudden loss in the process of switching the patient's visual distance between the far visual distance and the middle visual distance, and/or between the middle visual distance and the near visual distance, so that the patient can still see clear views during the switching process of the visual distances. When the location of the shift focus is lower than the lower limit of the range, the diffusion of the light energy is not obvious, so that it is difficult to solve the problem of sudden loss of vision. When the location of the shift focus is higher than the upper limit of the range, it is easy to cause the focus to shift excessively, resulting in a situation where the distribution of the light energy is still insufficient in the range between the expected focus and the shift focus, and accordingly there still exists the problem of sudden loss of vision.

With reference to FIGS. 3 to 5, in a specific embodiment, the focusing diffraction region 112 is provided with a first focusing diffraction structure 1121 and a second focusing diffraction structure 1122 with different heights. A first diffraction order of the first focusing diffraction structure 1121 provides a far distance visual focus corresponding to the far distance vision, and a third diffraction order of the first focusing diffraction structure 1121 provides a near distance visual focus corresponding to the near distance vision. Meanwhile, a second diffraction order of the first focusing diffraction structure 1121 is paired with a first diffraction order of the second focusing diffraction structure 1122 to provide the middle distance visual focus for the middle distance vision. Correspondingly, the shifting diffraction region 114 is provided with a first shifting diffraction structure 1141 and a second shifting diffraction structure 1142. The first shifting diffraction structure 1141 corresponds to the first focusing diffraction structure 1121, and the height ratio of the first shifting diffraction structure 1141 to the first focusing diffraction structure 1121 ranges from 1.1 to 1.3, that is, h3/h1 in FIG. 4 ranges from 1.1 to 1.3. The second shifting diffraction structure 1142 corresponds to the second focusing diffraction structure 1122, and the height ratio of the second shifting diffraction structure 1142 to the second focusing diffraction structure 1122 ranges from 1.1 to 1.3, that is, h4/h2 in FIG. 4 ranges from 1.1 to 1.3. Referring to a focus distribution shown in FIG. 5, in the embodiment, the above design may allow a shift focus generated by the shifting diffractive structure 1140 to be located in the range between the focus corresponding to the far distance vision and the focus corresponding to the middle distance vision (for example, the shift focus A is located in the range between the far distance visual focus and the middle distance visual focus, but overall closer to the far distance visual focus, as shown in FIG. 5), and allow the shift focus to be located in the range between the focus corresponding to the middle distance vision and the focus corresponding to the near distance vision (for example, the shift focuses B and C are located in the range between the middle distance visual focus and the near distance visual focus, but overall closer to the middle distance visual focus, as shown in FIG. 5), so that the light energy originally concentrated around the expected far distance visual focus and the middle distance visual focus can be partially diffused in space among the expected far distance visual focus, middle distance visual focus and near distance visual focus, thereby contributing to improve the vision of the patient in the process of switching the patient's visual distance from the expected far visual distance to the expected middle visual distance, and from the expected middle visual distance to the expected near visual distance, and avoiding the phenomenon of sudden loss of vision.

For the above embodiments, each first focusing diffraction structure 1121 matching the corresponding structure of the lens body 110 can cause the incident light with the designed wavelength to form a phase difference and coherence enhancement to form a plurality of diffraction orders, such as the first diffraction order, the second diffraction order, the third diffraction order, etc. The first diffraction order focus of each first focusing diffraction structure 1121 overlaps with each other to form the far distance visual focus, and the second diffraction order focus of each first focusing diffraction structure 1121 overlaps with each other to form the middle distance visual focus, and the third diffraction order focus of each first focusing diffraction structure 1121 overlaps with each other to form the near distance visual focus. The first diffraction order focus of the second focusing diffraction structure 1122 overlaps with the second diffraction order focus of each first focusing diffraction structure 1121 to jointly form the middle distance visual focus.

However, it should be noted that in other embodiments, the first diffraction order of the second focusing diffraction structure 1122 may also be paired with the third diffraction order of the first focusing diffraction structure 1121 to provide the near distance visual focus corresponding to the near distance vision, or the first diffraction order of the second focusing diffraction structure 1122 is paired with the first diffraction order of the first focusing diffraction structure 1121 to provide the far distance visual focus for the far visual distance. Particularly, it is possible to simultaneously allow the first diffraction order of the second focusing diffraction structure 1122 to be paired with the first diffraction order of the first focusing diffraction structure 1121 to provide the far distance visual focus, allow the second diffraction order of the second focusing diffraction structure 1122 to be paired with the second diffraction order of the first focusing diffraction structure 1121 to provide the middle distance visual focus, and allow the third diffraction order of the second focusing diffraction structure 1122 to be paired with the third diffraction order of the first focusing diffraction structure 1121 to provide the near distance visual focus.

Based on the aforementioned embodiments, a third shifting diffraction structure 1140 (not shown) may further be provided in the shifting diffraction region 114. The height ratio of the third shifting diffraction structure 1140 to the first focusing diffraction structure 1121 or the second focusing diffraction structure 1122 may range from 0.80 to 0.95. By cooperating with the design of the aforementioned embodiments, this design contributes to further balance the distribution of the light energy among the expected far distance visual focus, middle distance visual focus and near distance visual focus, not only enabling the patient to have better vision in the process of switching the patient's visual distance from the far visual distance to the middle visual distance and from the middle visual distance to the near visual distance, but also enabling the patient to have better vision in the process of switching the patient's visual distance from the near visual distance to the middle visual distance and from the middle visual distance to the far visual distance. In combination with the above design, the vision of the patient is less prone to sudden loss in the visual space between the maximum expected visual distance and the minimum expected visual distance.

Figure 6:
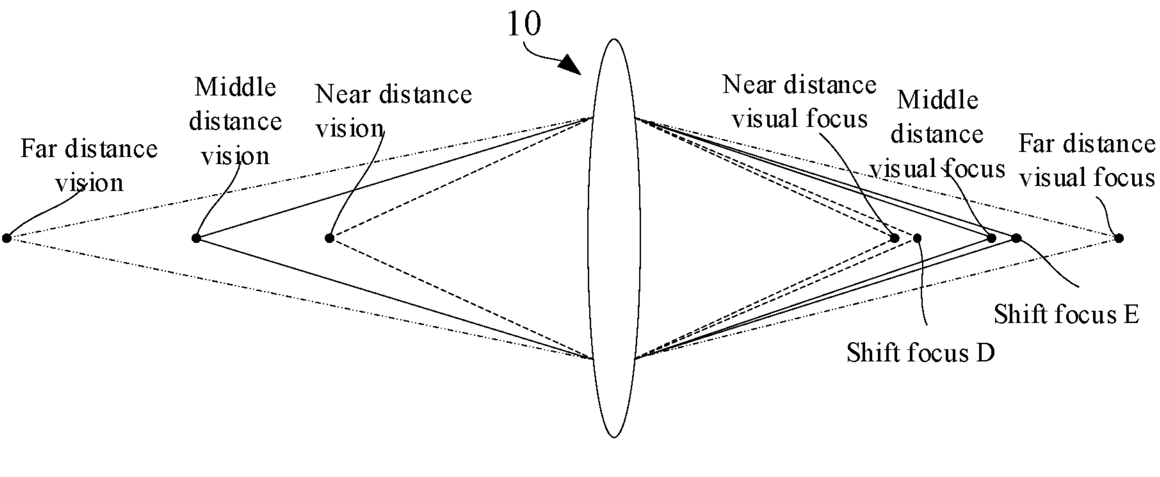
FIG. 6 is a schematic diagram illustrating relative positions of three focuses and shift focuses of the intraocular lens according to another embodiment of the present disclosure.

Referring to FIG. 6, specifically, when the third shifting diffraction structure 1140 corresponds to the above-mentioned first focusing diffraction structure 1121, partial light energy originally located at the middle distance visual focus and the near distance visual focus can be diffused towards the far distance visual focus and the middle distance visual focus respectively (As shown in FIG. 6, the shift focus E is located in the range between the middle distance visual focus and the far distance visual focus, but the shift focus E overall closer to the middle distance visual focus. The shift focus D is located in the range between the near distance visual focus and the middle distance visual focus, but the shift focus D overall closer to the near distance visual focus), so that the vision of the patient is not prone to sudden loss in the whole switching process of the visual distance from the near visual distance to the far visual distance. Correspondingly, when the third shifting diffraction structure 1140 corresponds to the above-mentioned second focusing diffraction structure 1122, partial light energy originally located at the middle distance visual focus can be diffused towards the far distance visual focus, so that the vision of the patient is not prone to sudden loss in the switching process of the visual distance from the middle visual distance to the far visual distance.

In some embodiments, the shifting diffraction region 114 may include at least two types of shifting diffraction structures 1140 with different heights, and the shifting diffraction structures 1140 with different heights are arranged alternately in sequence. Such design may contribute to improving the concentration of the light energy at the shift focus and further reduce the patient's sensitivity to the sudden loss in vision during the switching of the visual distances.

In addition, in some embodiments, the focus corresponding to the second diffraction order of the first shifting diffraction structure 1141 overlaps with the focus corresponding to the first diffraction order of the second shifting diffraction structure 1142. Such design may contribute to improving the distribution intensity of the light energy at the shift focus, thereby further improving the clarity of the scene seen by the patient during the switching from the middle visual distance to the near visual distance, and further avoiding the sudden loss in vision during the switching process.

On the other hand, in addition to controlling the height ratio of the shifting diffraction structure 1140 to the focusing diffraction structure 1120 in order to reduce the sudden loss of vision during the switching of the visual distances, in an embodiment of the present disclosure, an area ratio of a focusing diffraction structure 112 to a shifting diffraction region 114 is controlled, such that the patient can maintain the good vision for the scene within the original expected visual distance range, that is, the clarity of scene in other visual distance regions is further controlled while ensuring that the patient can at least obtain clear vision within the expected far, middle, and near visual distance ranges.

Figure 7:
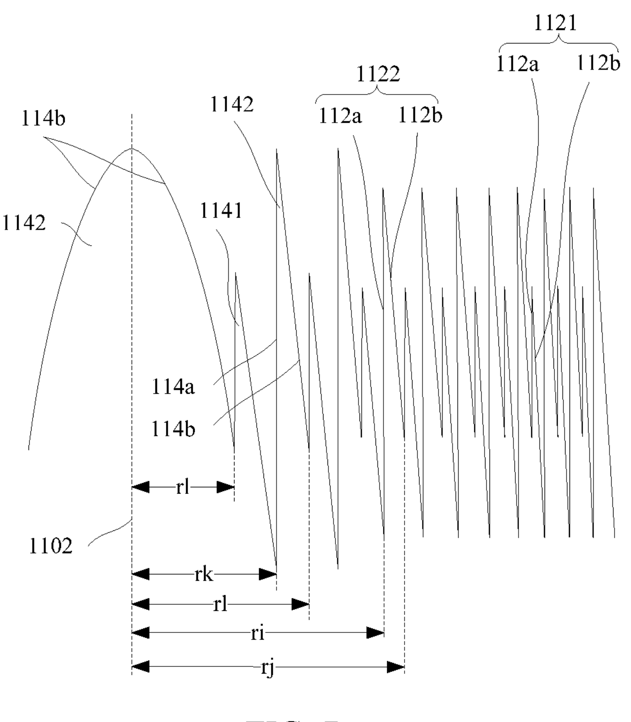
FIG. 7 is a schematic diagram illustrating a partial arrangement of a focusing diffraction structure and a shifting diffraction structure of an intraocular lens according to an embodiment of the present disclosure.

For the areas of the shifting diffraction region 114 and the focusing diffraction region 112, reference can be made to FIG. 7. Specifically, the focusing diffraction structure 1120 and the shifting diffraction structure 1140 are respectively rotationally symmetrical with respect to the optical axis 1102 of the lens body 110. The minimum distance from the focusing diffraction structure 1120 to the optical axis 1102 is defined as ri, and the maximum distance from the same focusing diffraction structure 1120 to the optical axis 1102 is defined as rj. Accordingly, the area of the focusing diffraction structure 1120 is $\pi(rj^2-ri^2)$. The sum of the areas of various focusing diffraction structures 1120 is equal to the area of the focusing diffraction region 112. The minimum distance from the focusing diffraction structure 1140 to the optical axis 1102 is defined as rk, and the maximum distance from the same focusing diffraction structure 1140 to the optical axis 1102 is defined as rl. Accordingly, the area of the shifting diffraction structure 1140 is $\pi(rl^2-rk^2)$, and the sum of the areas of various shifting diffraction structures 1140 is equal to the area of the shifting diffraction region 114. Particularly, for a diffraction structure through which the optical axis 1102 passes (the shifting diffraction structure 1140 in FIG. 7 is taken as an example), the minimum distance to the optical axis 1102 is 0, so that the area of the structure can be simplified to $\pi*rl^2$. Further, the area ratio of the shifting diffraction region 114 to the focusing diffraction region 112 ranges from 0.21 to 0.33. Specifically, the area ratio of the shifting diffraction region 114 to the focusing diffraction region 112 may be 0.23, 0.25, 0.27, 0.29, or 0.31. Such design can reasonably control the proportion of the transmitted light energy obtained by the shifting diffraction structure 1140 and the focusing diffraction structure 1120, so that the light energy around the expected visual distance can still occupy a larger proportion, that is, the patient can always have better visual acuity when the patient's visual distance is within the range of the expected visual distances, while the diffusion of the light energy in the space among the expected far, middle and near visual distances is also taken into account, thereby further increasing the visual clarity of the patient when the patient's visual distance is within the range of the expected visual distances. When below the lower limit of the relationship, the area ratio of the shifting diffraction region 114 is too low, and the light energy corresponding to the expected visual distance is not significantly diffused between the expected focuses, accordingly it is difficult to improve the sudden loss in vision; and when above the upper limit of the relationship, the area ratio of the shifting diffraction region 114 is too large, and the light energy corresponding to the original expected visual distance is diffused too much, which in turn leads to a significant loss in visual acuity at the originally ideal expected visual distance.

Referring to FIG. 4, in an embodiment, the focusing diffraction region 112 is located at the periphery of the shifting diffraction region 114, the focusing diffraction region 112 and the shifting diffraction region 114 are single continuous regions and connected to each other, where r1 is defined as the maximum outer ring radius of the shifting diffraction region 114, r2 is defined as the maximum outer ring radius of the focusing diffraction region 112, both of which satisfy the relationship 0.21≤r12/(r22-r12)≤0.33.

In an embodiment, the focusing diffraction region 112 is located at the periphery of the shifting diffraction region 114, an inner ring of the focusing diffraction region 112 is connected to an outer ring of the shifting diffraction region 114, and the shifting diffraction region 114 includes the shifting diffraction structure 1140 through which the optical axis 1102 passes. The outer ring radius of the shifting diffraction region 114 is less than or equal to 1.5 mm, and the outer ring radius of the focusing diffraction region 112 is less than or equal to 3 mm. By the radius design and the aforementioned region ratio relationship, the focusing diffraction region 112 can obtain no less than 75% of the transmitted light energy, while the shifting diffraction region 114 can obtain less than 25% of the transmitted light energy, thereby ensuring the visual clarity in the ranges of the expected far visual distance, middle visual distance and near visual distance.

The above embodiment mainly describes that the focusing diffraction region 112 is located at the periphery of the shifting diffraction region 114. However, in fact, the shifting diffraction region 114 in the embodiment of the present disclosure may also be provided at the periphery of the focusing diffraction region 112. The inner ring of the shifting diffraction region 114 is connected to the outer ring of the focusing diffraction region 112, and the focusing diffraction region 112 includes the focusing diffraction structure 1120 through which the optical axis 1102 passes. The outer ring radius of the focusing diffraction region 112 is greater than or equal to 2.5 mm, and the outer ring radius of the shifting diffraction region 114 is less than or equal to 3 mm.

The above two specific designs can both reasonably control the proportional relationship between the light energy and the diffused light energy at the expected visual distance, and can reasonably control the proportion of the transmitted light energy obtained by the shifting diffraction structure 1140 and the focusing diffraction structure 1120, so that the patient can always have better visual acuity when the patient's visual distance is within the range of the expected visual distances, and meanwhile the visual clarity of the patient when the visual distance of the patient is in the range of the expected visual distances is ensured.

In addition, in some embodiments, the spherical aberration of the intraocular lens 10 is between 0.15 μm and 0.2 μm, which can not only correct the spherical aberration inherent in the human eye, but also reserve a certain global aberration to increase the depth of focus and strengthen the continuity of the visual range, so that the position in the range between the focuses may also provide good visual quality and reduce glare.

The intraocular lens 10 in the embodiment of the present disclosure may be configured to replace partial natural lens in the human eye. Accordingly, referring to FIGS. 1 and 2, in some embodiments, the intraocular lens 10 may include a pair of haptics 120, and the haptics 120 are connected to the lens body 110 to fix the lens body 110 in the capsular bag of the human eye to ensure that the lens body 110 may not deflect or move within the human eye. The haptics 120 and the lens body 110 may be formed in one piece.

For the embodiment of the present disclosure, either of the side surfaces of the lens body 110 can be aspherical or spherical. The lens body 110 is mainly configured to correct the inherent spherical aberration in the human eye according to the size of the spherical aberration of the human eye. The aspheric surface type is represented is as follows:

$$Z(r) = \frac{r^2}{R\left\{1 + \sqrt{1 - (1+k)\left(\frac{r^2}{R^2}\right)}\right\}} + \alpha_1 r^4 + \alpha_2 r^6 + \ldots + \alpha_n r^{(2n+2)};$$

where Z(r) represents an aspheric surface type function, r denotes a radial coordinate (equal to a distance from a center point of the lens to the optical axis), R denotes a curvature radius of a basic spherical surface, k denotes a quadratic surface coefficient, a denotes an aspherical high-order term coefficient, i=1, 2, . . . , n, where n is a natural number greater than or equal to 1. When k=0 and the aspherical high-order term coefficient ai are all equal to 0, the corresponding surface type is a spherical surface.

For a continuous optical surface type, a continuous phase function thereof is as follows:

$$\Phi(r) = (2\pi/\lambda_0)(n_1 - n_2)Z(r);$$

where r denotes the radial coordinate, $\lambda_0$ denotes the design wavelength, $n_1$ denotes a refractive index of a material of the intraocular lens corresponding to light wave with the wavelength $\lambda_0$, and $n_2$ denotes a refractive index of the surrounding environment of the intraocular lens (for example, the aqueous humor of the human eye) corresponding to the light wave with the wavelength $\lambda_0$, Z(r) represents a surface type function of the surface.

In some embodiments, the optical refractive index of the material of the intraocular lens 10 ranges from 1.45 to 1.55 at 35° C., and the Abbe number (i.e., "diffusion coefficient") ranges from 45 to 55. For example, the material of the intraocular lens 10 may be hydrophilic acrylate, hydrophobic acrylate, silica gel, polymethylmethacrylate (PMMA), etc. The lens body 110 in the intraocular lens 10 and the focusing diffraction structures 1120 and the shifting diffraction structures 1140 are formed in one piece.

For a given continuous phase function Φ(r), manufacturing of a diffraction structure requires phase compression and layering. A compressed phase value determines a height of a step in a diffraction profile (that is, the height of the step surface in the direction parallel to the optical axis). The height of the steps is as follows:

$$h = \Delta\Phi\frac{\lambda_0}{(2\pi)(n_1 - n_2)};$$

where ΔΦ denotes a phase difference caused by the step to the incident light.

The diffraction structure is provided with a plurality of diffraction steps, and the ring radius of each diffraction step is as follows:

$$r_j = \sqrt{2j\lambda_0 f};$$

where η denotes the step number, and f denotes the +1-st order diffraction focal length.

Diffraction efficiencies of different orders of the diffraction structure are as follows:

$$\eta = \mathrm{sinc}^2\left(\pi\left(\frac{\lambda_0}{\lambda}\frac{n(\lambda)-1}{n(\lambda_0)-1} - m\right)\right);$$

where η denotes the diffraction efficiency, m denotes the diffraction order, λ denotes an actual wavelength, $n(\lambda_0)$ and $n(\lambda)$ denote refractive indexes of the material at the designed wavelength and the actual wavelength respectively.

Focusing diffraction structures 11120 with different heights have different first diffraction orders, for example, a first diffraction order focal length of a focusing diffraction structure 1120 with one height is f1, a first diffraction order focal length of a focusing diffraction structure 1120 with another height is f2, and a first diffraction order focal length of a focusing diffraction structure 1120 with further another height is f3. In some embodiments, there exists an integer multiple relationship among the focal lengths corresponding to the first diffraction orders of the focusing diffraction structures 1120 with different heights, such as f2=2f1, f3=3f1, and the focusing diffraction structures 1120 with different heights are arranged alternately. Accordingly, the focuses provided by the focusing diffraction structures 1120 overlap with each other, thereby contributing to obtaining the desired distribution of the light energy.

A specific embodiment is taken as an example to describe the intraocular lens 10 provided by the present disclosure as follows.

Referring to FIG. 7, in an embodiment, the intraocular lens 10 is a trifocal lens, in which the refractive index of the lens body 110 and each diffractive structure is equal to 1.54, and one side surface of the lens body 110 is provided with a continuous focusing diffraction region 112 and a continuous shifting diffraction region 114. The focusing diffraction region 112 is connected to the shifting diffraction region 114 and is located at the periphery of the shifting diffraction region 114. The outer ring radius of the shifting diffraction region 114 is equal to 1.483 mm, and the area ratio of the shifting diffraction region 114 to the focusing diffraction region 112 is equal to 0.244. That is, approximately 75% of the light energy can be obtained around the desired focuses determined by the focusing diffraction region 112, and the remaining approximately 25% of the light energy can be obtained around the shift focus determined by the shifting diffraction region 114.

The focusing diffraction region 112 is provided with a first focusing diffraction structure 1121 with a height h1 and a second focusing diffraction structure 1122 with a height h2 arranged alternately in sequence. A height ratio h1:h2 of the first focusing diffraction structure 1121 to the second focusing diffraction structure 1122 is equal to 1:2. In the embodiment, there are eight first focusing diffraction structures 1121 and eight second focusing diffraction structures 1122, and there are two first shifting diffraction structures 1141 and three second shifting diffraction structures 1142. The first diffraction order of the first focusing diffraction structure 1121 provides a far distance visual focus corresponding to the far distance vision, and the third diffraction order of the first focusing diffraction structure 1121 provides a near distance visual focus corresponding to the near distance vision. Meanwhile, the second diffraction order of the first focusing diffraction structure 1121 is paired with the first diffraction order of the second focusing diffraction structure 1122 to provide a middle distance visual focus corresponding to the middle distance version. The shifting diffraction region 114 is provided with a first shifting diffraction structure 1141 with a height h3 and a second shifting diffraction structure 1142 with a height h4 arranged alternately in sequence. The first shifting diffraction structure 1141 corresponds to the first focusing diffraction structure 1121, and the height ratio h3:h1 of the height of the first shifting diffraction structure 1141 to the height of the first focusing diffraction structure 1121 is equal to 1.107. The second shifting diffraction structure 1142 corresponds to the second focusing diffraction structure 1122, and the height ratio h4:h2 of the height of the second shifting diffraction structure 1142 to the height of the second focusing diffraction structure 1122 is also equal to 1.107. The shift focus formed by the first diffraction order of the first shifting diffraction structure 1141 provides a greater depth of field for the far distance vision in a region of the far distance visual focus approaching the middle distance visual focus, and accordingly, smooth transition of the vision in the process of switching from the far distance vision to the middle distance vision can be implemented. A shift focus corresponding to the second diffraction order of the first shifting diffraction structure 1141 overlaps with a shift focus corresponding to the first diffraction order of the second shifting diffraction structure 1142, and the shift focuses formed by the two diffraction orders are located in a region of the middle distance visual focus approaching the near distance visual focus, and accordingly, ranges of the depth of field between the middle distance vision and the near distance vision can be better connected to each other, thereby implementing the successive changeable focus in the process of switching from the middle distance vision to the near distance vision.

A basic focal power brought by the lens body 110 in the embodiment is +20 D, and the additional focal power provided by the focusing diffractive structure 1120 on the lens body 112 for the middle distance vision is +1.66 D, which may correspond to the middle visual distance of about 80 cm. This visual distance can correspond to a distance between the human eye and a computer. The additional focal power of the focusing diffraction structure 1120 for the near distance vision is +3.33 D, which may correspond to the near visual distance of about 40 cm, which can correspond to a distance between the human eye and a book, or a mobile phone.

Figure 8:
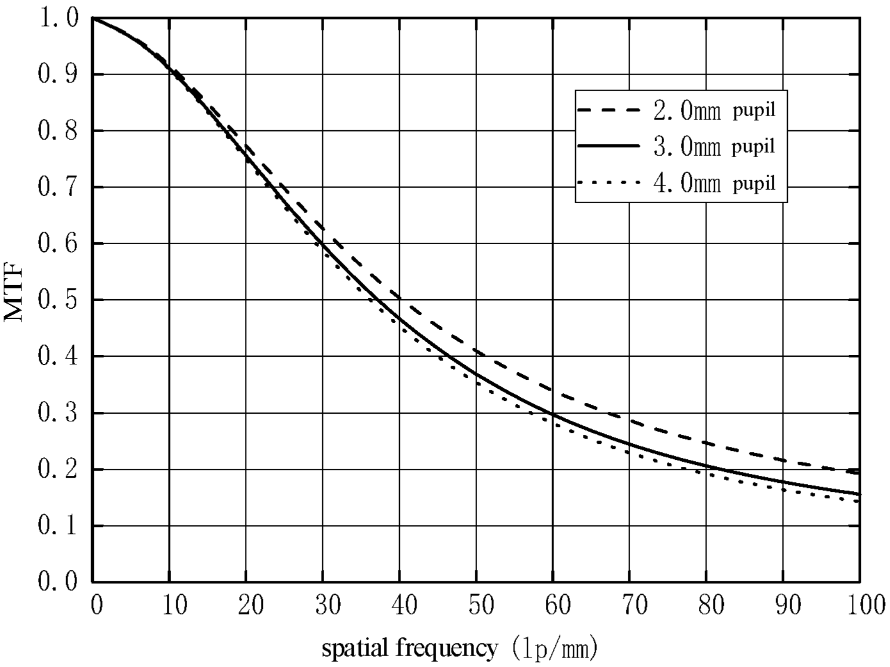
FIG. 8 is a curve graph of a modulation transfer function with a spatial frequency under different pupil sizes after an intraocular lens is introduced into an eye model according to an embodiment of the present disclosure.

For the intraocular lens 10 of the embodiment, since a coverage range of each first diffraction surface **112*b* on the first focusing diffraction structure 1121 and the second focusing diffraction structure 1122 includes most of the peripheral region on the lens body 110, so that the focus distribution of the intraocular lens 10 is not easily affected by the pupil size, and accordingly, there is little difference in the patient's visual quality under the dark environment and the bright environment. Referring to FIG. 8, it shows a curve graph of a modulation transfer function (MTF) with a spatial frequency under different pupil sizes after the intraocular lens 10 is introduced into an eye model (the eye model complies with the relevant requirements in ISO11979-2). It can be seen from FIG. 8 that the MTFs of the intraocular lens 10 in the embodiment under 2.0 mm, 3 mm and 4.5 mm pupils are not much different. Accordingly, the visual quality of the intraocular lens 10** in the embodiment is less affected by the pupil.

Figure 9:
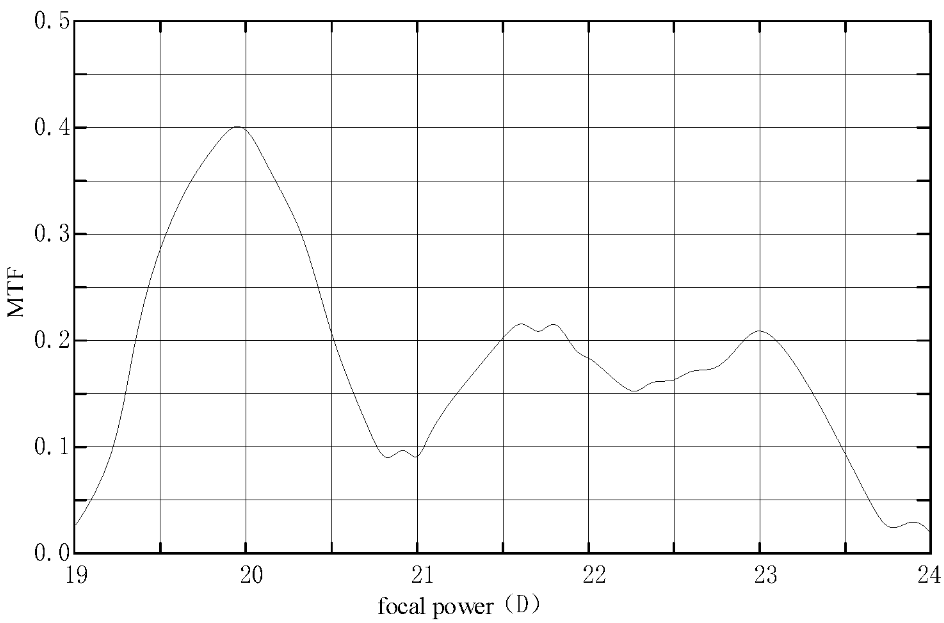
FIG. 9 shows a modulation transfer function for 50 lp/mm measured at different focal powers after an intraocular lens is introduced into an eye model according to an embodiment of the present disclosure.

FIG. 9 shows a variation curve for 50 lp/mm measured at different focal powers after an intraocular lens is introduced into an eye model (the eye model complies with the relevant requirements in ISO11979-2). As can be seen from FIG. 9, values of the MTF of the intraocular lens 10 at the far distance visual focus, the middle distance visual focus, and the near distance visual focus are 0.40, 0.22, and 0.21 respectively, which are higher than the MTF standard value of the multifocal intraocular lens 10 (the MTF value of the multifocal intraocular lens 10 should be greater than 0.2 according to the standard requirements). In the intraocular lens 10 of the embodiment, the light energy distributed at the far distance visual focus ranges from 35% to 50% of the total transmitted light energy, the light energy distributed at the middle distance visual focus ranges from 15% to 30% of the total transmitted light energy, and the light energy distributed at the near distance visual focus ranges from 20% to 35% of the total transmitted light energy. In addition, the additional focal power of the focusing diffraction structure 1120 in the embodiment for the middle distance vision is +1.66 D, which may correspond to the middle visual distance of about 80 cm, and the visual distance may correspond to a distance between the human eye and the computer. The additional focal power of the focusing diffraction structure 1120 for the near distance vision is +3.33 D, which may correspond to the near visual distance of about 40 cm, and the visual distance may correspond to the distance between the human eye and a book or a mobile phone. Moreover, by the above-mentioned shifting diffraction region 114, the depth of field between focuses can be reasonably increased, so that the lens can also obtain good vision in the space between two focuses.

It can also be seen from the analysis in FIG. 9 that in the embodiment, particularly for the continuous visual range from the middle visual distance to the near visual distance, the MTF value at any position in the visual range of 25 cm to 80 cm is greater than 0.1, thereby implementing the successive changeable focus in the visual range of 25 cm to 80 cm, so that the patient using the intraocular lens 10 may obtain more comfortable experience when switching among using a computer, checking a mobile phone, and reading a book, and postoperative glasses removal can be indeed achieved.

Figure 10:
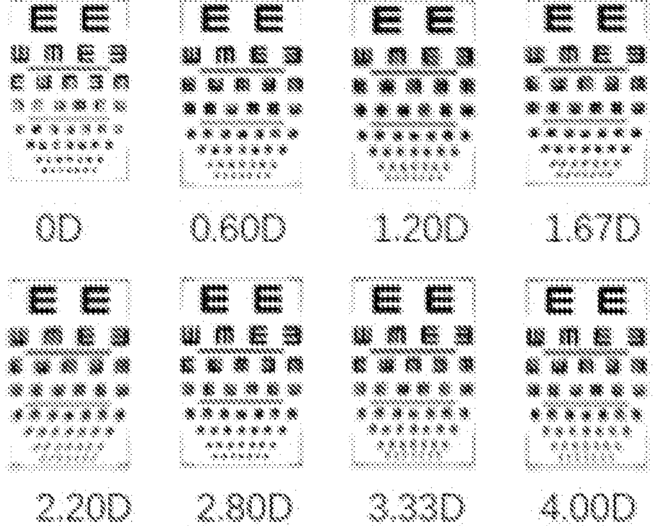
FIG. 10 shows visual acuity test charts for different object distances after an intraocular lens is introduced into an eye model according to an embodiment of the present disclosure.

FIG. 10 shows a visual acuity chart detection diagram for different object distances after an intraocular lens is introduced into an eye model according to an embodiment (the eye model complies with the relevant requirements in ISO11979-2), where OD represents a visual distance at infinity, which corresponds to the fat distance vision, 1.67 D represents the middle distance vision, and 3.33 D represents the near distance vision. The intraocular lens 10 in the embodiment performs better than the conventional trifocal intraocular lens 10 in terms of clarity continuity in the range of the middle visual distance to the near visual distance.

With the intraocular lens provided in the embodiments of the present disclosure, the patient's visual acuity is not prone to significant sudden loss when the patient's visual distance is switched between the far visual distance and the middle visual distance, and/or between the middle visual distance and the near visual distance, thereby providing a smooth transition of vision when switching among different visual distances, improving the patient's vision balance among the expected far, middle and near visual distances, and further contributing to improve the patient's postoperative experience.

The technical features of the above-described embodiments can be combined in any way. To simplify the description, all possible combinations of the technical features in the above-described embodiments are not described. However, as long as there is no contradiction in the combinations of these technical features, all should be considered to be within the scope of the present disclosure.

The above-mentioned embodiments are merely some exemplary embodiments of the present disclosure, and the descriptions thereof are more specific and detailed, but they should not be understood as limiting the scope of the present disclosure. It should be noted that, those of ordinary skill in the art can make a number of modifications and improvements without departing from the concept of the present disclosure, which all fall within the protection scope of the present disclosure. Therefore, the protection scope of the present disclosure shall be subject to the appended claims.

The invention claimed is:

1. An intraocular lens, comprising:

a lens body, at least one side surface of the lens body being provided with a focusing diffraction region comprised by a series of annular, concentric echelettes and a radially-adjacent shifting diffraction region comprised by a series of annular, concentric echelettes, wherein the focusing diffraction region comprises at least two types of focusing diffraction structures with different heights, and the focusing diffraction structures with different heights are arranged alternately to provide the intraocular lens with focuses corresponding to a far distance vision, a middle distance vision and a near distance vision respectively;

the shifting diffraction region comprises shifting diffraction structures corresponding to the focusing diffraction structures; and wherein a height ratio of at least one type of the shifting diffraction structures to one corresponding type of the focusing diffraction structures ranges from 1.1 to 1.3, or from 0.80 to 0.95, the shifting diffraction structures are configured to provide a shift focus for the intraocular lens, the shift focus is located in a range between the focus corresponding to the far distance vision and the focus corresponding to the middle distance vision, and/or in a range between the focus corresponding to the middle distance vision and the focus corresponding to the near distance vision, wherein one type of the focusing diffraction structures is configured to provide a far distance visual focus corresponding to the far distance vision and/or a middle distance visual focus corresponding to the middle distance vision, and a height ratio of one corresponding type of the shifting diffraction structures to the focusing diffraction structure providing the far distance visual focus and/or the middle distance visual focus ranges from 1.1 to 1.3, wherein the shifting diffraction region is located at a periphery of the focusing diffraction region, an inner ring of the shifting diffraction region is connected to an outer ring of the focusing diffraction region, and the focusing diffraction region comprises a focusing diffraction structure through which an optical axis of the lens body passes and a focusing diffraction structure spaced apart from the optical axis, wherein the focusing diffraction structure spaced apart from the optical axis is provided with a first step surface facing the optical axis and a first diffraction surface facing away from the optical axis, one end of the first step surface of the focusing diffraction structure is configured to be connected to the first diffraction surface of the focusing diffraction structure, the other end is configured to be connected to a diffraction surface of an adjacent focusing diffraction structure or an adjacent shifting diffraction structure, there exists an abrupt change in the surface type at a connection between surfaces, the focusing diffraction structure through which the optical axis passes is provided with a first diffraction surface, wherein the at least two types of focusing diffraction structures with different heights comprise a first focusing diffraction echelette and a second focusing diffraction echelette, wherein the shifting diffraction structures comprises a first shifting diffraction echelette and a second shifting diffraction echelette;

the first shifting diffraction echelette corresponds to the first focusing diffraction echelette; and the second shifting diffraction echelette corresponds to the second focusing diffraction echelette.

2. The intraocular lens according to claim 1, wherein a first diffraction order of the first focusing diffraction echelette is configured to provide a far distance visual focus for the far distance vision, a second diffraction order of the first focusing diffraction echelette is paired with a first diffraction order of the second focusing diffraction echelette to provide a middle distance visual focus for the middle distance vision, and a third diffraction order of the first focusing diffraction echelette is configured to provide a near distance visual focus for the near distance vision.

3. The intraocular lens according to claim 1, wherein a first diffraction order of the first focusing diffraction echelette is paired with a first diffraction order of the second focusing diffraction echelette to provide a far distance visual focus for the far distance vision, a second diffraction order of the first focusing diffraction echelette is configured to provide a middle distance visual focus for the middle distance vision, and a third diffraction order of the first focusing diffraction echelette is configured to provide a near distance visual focus for the near distance vision.

4. The intraocular lens according to claim 1, wherein a first diffraction order of the first focusing diffraction echelette is configured to provide a far distance visual focus for the far distance vision, a second diffraction order of the first focusing diffraction echelette is configured to provide a middle distance visual focus for the middle distance vision, and a third diffraction order of the first focusing diffraction echelette is paired with a first diffraction order of the second focusing diffraction echelette to provide a near distance visual focus for the near distance vision.

5. The intraocular lens according to claim 1, wherein a first diffraction order of the first focusing diffraction echelette is paired with a first diffraction order of the second focusing diffraction echelette to provide a far distance visual focus for the far distance vision, a second diffraction order of the first focusing diffraction echelette is paired with a second diffraction order of the second focusing diffraction echelette to provide a middle distance visual focus for the middle distance vision, and a third diffraction order of the first focusing diffraction echelette is paired with a third diffraction order of the second focusing diffraction echelette to provide a near distance visual focus for the near distance vision.

6. The intraocular lens according to claim 1, a height ratio of the first shifting diffraction echelette to the first focusing diffraction echelette ranges from 1.1 to 1.3; and a height ratio of the second shifting diffraction echelette to the second focusing diffraction echelette ranges from 1.1 to 1.3.

7. The intraocular lens according to claim 1, wherein the first and second shifting diffraction echelettes comprise different heights, and the shifting diffraction echelettes with different heights are arranged alternately in sequence.

8. The intraocular lens according to claim 1, wherein the focusing diffraction echelettes and the shifting diffraction echelettes are respectively rotationally symmetrical with respect to the optical axis of the lens body, and a ratio of an area of the shifting diffraction region to an area of the focusing diffraction region ranges from 0.21 to 0.33;

wherein the area of the focusing diffraction region is a sum of areas of the focusing diffraction echelettes, and an area of each of the focusing diffraction echelettes is represented as $\pi(rj^2-ri^2)$, where ri denotes the minimum distance from the focusing diffraction echelette to the optical axis, and rj denotes the maximum distance from the same focusing diffraction echelette to the optical axis; and wherein the area of the shifting diffraction region is a sum of areas of the shifting diffraction echelettes, and an area of each of the shifting diffraction echelettes is represented as $\pi(rl^2-rk^2)$, where rk denotes the minimum distance from the shifting diffraction echelette to the optical axis, and rl is the maximum distance from the same shifting diffraction echelette to the optical axis.

9. The intraocular lens according to claim 1, wherein a focal power of the lens body ranges from −10 D to +36 D, an additional optical power of the focusing diffraction echelette for the near distance vision ranges from +3.00 D to +4.34 D, and an additional optical power of the focusing diffraction echelette for the middle distance vision ranges from +1.50 D to +2.17 D.

10. The intraocular lens according to claim 1, wherein there exists an integer multiple relationship among focal lengths corresponding to the first diffraction orders of the focusing diffraction echelettes with different heights.

11. The intraocular lens according to claim 1, further comprising a pair of haptics connected to the lens body.

* * * * *